United States Patent
Pojman

(10) Patent No.: US 11,186,659 B2
(45) Date of Patent: Nov. 30, 2021

(54) CURE-ON-DEMAND AND TIME-LAPSE POLYMERIZATION

(71) Applicant: John Anthony Pojman, Baton Rouge, LA (US)

(72) Inventor: John Anthony Pojman, Baton Rouge, LA (US)

(73) Assignee: BOARD OF SUPERVISORS OF LOUISIANA STATE UNIVERSITY AND AGRICULTURAL AND MECHANICAL COLLEGE, Baton Rouge, LA (US)

( * ) Notice: Subject to any disclaimer, the term of this patent is extended or adjusted under 35 U.S.C. 154(b) by 227 days.

(21) Appl. No.: 16/197,545

(22) Filed: Nov. 21, 2018

(65) Prior Publication Data

US 2019/0153130 A1 May 23, 2019

Related U.S. Application Data

(60) Provisional application No. 62/589,593, filed on Nov. 22, 2017.

(51) Int. Cl.
| | |
|---|---|
| C08F 16/06 | (2006.01) |
| C08G 59/40 | (2006.01) |
| C08G 59/22 | (2006.01) |
| C08K 5/55 | (2006.01) |
| C12N 9/80 | (2006.01) |
| C08K 3/38 | (2006.01) |
| C08G 59/62 | (2006.01) |

(52) U.S. Cl.
CPC ............ *C08F 16/06* (2013.01); *C08G 59/22* (2013.01); *C08G 59/4021* (2013.01); *C08G 59/4028* (2013.01); *C08G 59/4064* (2013.01); *C08G 59/62* (2013.01); *C08K 3/38* (2013.01); *C08K 5/55* (2013.01); *C12N 9/80* (2013.01); *C08F 2810/20* (2013.01); *C08K 2003/387* (2013.01); *C12Y 305/01005* (2013.01)

(58) Field of Classification Search
CPC .... C08F 16/06; C08F 2810/02; C08F 216/06; C08G 59/4028; C08G 59/4046; C08G 59/4021; C08G 59/62; C08K 2003/387; C08K 3/38; C08K 5/55; C12N 9/80; C12Y 305/01005
See application file for complete search history.

(56) References Cited

U.S. PATENT DOCUMENTS

| 5,315,573 A | 5/1994 | Nakao | |
|---|---|---|---|
| 2005/0249891 A1* | 11/2005 | Kitamura | C08K 5/16 428/1.53 |
| 2007/0134459 A1* | 6/2007 | Hubert | G02B 1/105 428/40.1 |
| 2008/0268158 A1* | 10/2008 | Fugitt | D21H 23/56 427/373 |
| 2016/0369127 A1* | 12/2016 | Carlborg | C08G 59/4064 |

FOREIGN PATENT DOCUMENTS

JP 2014095071 A * 5/2014

OTHER PUBLICATIONS

Brandie et al. Polym. Chem. (2012) 3: 3224-3227 (Year: 2012).*
Machine translation of JP 2014095071 A (publication year 2014) downloaded from the EPO on Aug. 31, 2020 (Year: 2014).*
Bayramoglu et al., Activity and Stability of Urease Entrapped in Thermosensitive Poly(N-Isopropylacrylamide-Co-Poly(Ethyleneglycol)-Methacrylate) Hydrogel, Bioprocess and Biosystems Engineering 2014, 37, 235-243.
Bortone et al., Immobilization/Stabilization of Acid Urease on Eupergit Supports, Biotechnol. Prog., 2012, 28, 1232-1244.
D'Souza et al., Immobilization of the Urease on Eggshell Membrane and Its Application in Biosensor, Materials Science and Engineering: C 2013, 33, 850-854.
Datta et al., Enzyme Immobilization: An Overview on Technigues and Support Materials, 3 Biotech 2013, 3, 1-9.
Gianfreda and Scarfi, Enzyme Stabilization: State of the Art, Molecular and Cellular Biochemistry 1991, 100, 97-128.
Higham et al., Gelation and Crosslinking in Multi-Functional Thiol and Multi-Functional Acrylate Systems Involving an in Situ Comonomer Catalyst, Macromolecules 2014, 47, 821-829.
Hu et al., Base-Catalyzed Feedback in the Urea-Urease Reaction, J. Phys. Chem. B 2010, 114, 14059-14063.
Hu et al., Time-Lapse Thiol-Acrylate Polymerization Using a Ph Clock Reaction, J. Polym. Sci. Part A: Polym. Chem. 2010, 48, 2955-2959.
Iwakura and Okada, The Kinetics of the Tertiary-Amine-Catalyzed Reaction of Organic Isocyanates with Thiols, Can. J. Chem. 1960, 38, 2418-2424.
Jee et al., Temporal Control of Gelation and Polymerization Fronts Driven by an Autocatalytic Enzyme Reaction, Angew. Chem. 2016, 128, 2167-2171.
Krajewska et al., Probing Acid-Base Groups of the Active Site by pH Variation, Plant Physiol. Biochem. 2005, 43, 651-658.
Lewis et al., Isothermal Frontal Polymerization: Confirmation of the Mechanism and Determination of Factors Affecting Front Velocity, Front Shape, and Propagation Distance with Comparison to Mathematical Modeling, J. Polym. Sci. Part A Polym. Chem. 2005, 43, 5774-5786.
Luo and Fu, Immobilization of Urease on Dialdehyde Porous Starch, Starch—Stärke 2010, 62, 652-657.
MacChesney Scientific American 1997, 277, 96.
Marzadori et al., Immobilation of Jack Bean Urease on Hydroxyapatite: Urease Immobiization in Alkaline Soils, Soil Biol. Biochem. 1998, 30, 1485-1490 (abstract).
Mohapatra et al., Design of small molecule reagents that enable signal amplification via an autocatalytic, base-mediated cascade elimination reaction, Chem Commun. 2012, 48, 3018-20.

(Continued)

*Primary Examiner* — Susan M Hanley
(74) *Attorney, Agent, or Firm* — Riverside Law LLP

(57) ABSTRACT

The present invention provides compositions, methods and kits for the temporal control induction time for a polymerization reaction.

21 Claims, 8 Drawing Sheets

(56) References Cited

OTHER PUBLICATIONS

Morales and Pojman, A Study of the Effects of Thiols on the Frontal Polymerization and Pot Life of Multifunctional Acrylate Systems Initiated by Cumene Hydroperoxide, J. Polym. Sci. Part A: Polym. Chem. 2013, 51, 3850-3855.
Nabati et al., Dioxane Enhanced Immobilization of Urease on Alkyl Modified Nano-Porous Silica Using Reversible Denaturation Approach, Journal of Molecular Catalysis B: Enzymatic 2011, 70, 17-22 (abstract).
Parrinello et al., Thermal Frontal Polymerization with a Thermally Released Redox Catalyst, J. Polym. Sci. Part A: Polym. Chem. 2012, 50, 2337-2343.
Pojman, Frontal Polymerization: in Polymer Science: A Comprehensive Reference; Matyjaszewski ed., 2012; pp. 957-980.
Salgado, et al., Development of Potentiometric Urea Biosensor Based on Canavalia Ensiformis Urease; INTECH Open Access Publisher: 2011, 16 pages.
Smoak et al., Antimicrobial Cytocompatible Pentaerythritol Triacrylate-Co-Trimethylolpropane Composite Scaffolds for Orthopaedic Implants, J. Appl. Poly. Sci. 2014, 131, 41099, 7 pages.
Thoma, et al., Electron paramagnetic resonance measurement of trapped radical concentrations in frontally polymerized and bulk☐polymerized multifunctional (meth)acrylates, J Polymer Sci A:Polymer Chem 2011, 49:4261-66.
Wrobel et al., pH Wave-Front Propagation in the Urea-Urease Reaction, Biophysical J. 2012, 103, 610-615.

\* cited by examiner $B(OH)_3 + H_2O \rightleftharpoons B(OH)_4^- + H^+$

CURE-ON-DEMAND AND TIME-LAPSE POLYMERIZATION

CROSS-REFERENCE TO RELATED APPLICATIONS

This application claims priority from U.S. Provisional Application Ser. No. 62/589,593, filed on Nov. 22, 2017, which is incorporated by reference herein in its entirety.

STATEMENT REGARDING FEDERALLY SPONSORED RESEARCH OR DEVELOPMENT

This invention was made with government support under CBET 1511653 awarded by the National Science Foundation. The government has certain rights in the invention.

BACKGROUND OF THE INVENTION

There is much interest in the design of functional and adaptive polymer systems by the use of reaction networks under kinetic control. Gel lifetime has been controlled by tuning the timescale of competing self-assembly and disassembly processes by using enzyme catalysts, the in-situ formation of gelators, or the injection of promotors for self-assembly and/or deactivators for self-destruction. In these systems, gelation began immediately after the addition of the catalysts/fuel.

Many materials-chemistry applications, such as adhesives, coatings, sealants, and injectable biomedical formulations, require an initial slow reaction followed by rapid curing. An induction period before the rapid reaction can be introduced either through the consumption of an inhibitor that prevents the accumulation of products, for example, time-lapse polymerization was possible in a base-catalyzed thiol-Michael addition reaction by the use of acid inhibitors, or as the result of an initial slow evolution of a chemical species or heat.

Thermal feedback in polymerization is the ability to create cure-on-demand systems in which the formulation does not react until the external application of localized heating and then propagates as a constant-velocity (cm min$^{-1}$) polymerization front. Adhesives, for example, can be readily applied as a liquid or paste and then rapidly cured even in inaccessible locations by the propagation of the front from the initiation site. Frontal polymerization has also been used to create intricate endoskeletons in flexible materials. However, thermal frontal polymerization requires relatively thick layers and/or surfaces that are poor thermal conductors lest heat loss quench the propagation. It also involves large temperature changes (>100° C.).

There is thus a need in the art for compositions and methods for initial slow reaction followed by rapid curing of adhesive materials. The present invention addresses this unmet need in the art.

SUMMARY OF THE INVENTION

The present invention provides compositions for forming a polymer. In one embodiment, the composition comprises a polyhydroxy monomer, and a borate ion source. In one embodiment, the composition comprises an epoxy resin and a compound comprising one or more thiol groups. In one embodiment, the composition further comprises urea and at least one urease source.

In one embodiment, the polyhydroxy monomer is selected from the group consisting of poly(vinyl) alcohol (PVA), 1,4-butanediol, 1,6-hexanediol, ethylene glycol, 2-ethyl-1,3-hexanediol (EHD), 2-butyl-2-ethyl-1,3-propanediol (BEPG), 2,2,4-trimethyl-1,3-pentanediol (TMPD), 2,4-deithyl-1,5-pentanediol (PD-9), hydroquinone dihydroxyethyl ether (HQEE), diethylene glycol, propylene glycol, trimethylolpropane, and glycerol.

In one embodiment, the borate ion source is selected from the group consisting of boric acid, borax, calcium borate, sodium borate, sodium tetraborate, disodium tetraborate, and any combination there of.

In one embodiment, the epoxy resin is selected from the group consisting of ethylene glycol diglycidyl ether (EGDGE), n-butyl glycidyl ether (BGE), polypropylene glycol diglycidyl ether (PPGDGE), and polyethylene glycol diglycidyl ether (PEGDGE).

In one embodiment, the compound comprising one or more thiol groups is selected from the group consisting of pentaerythritol tetra(3-mercapto-propionate) (PETMP); trimethylol-propane tri(3-mercapto-propionate) (TMPMP); glycol di(3-mercapto-propionate) (GDMP); tris[25-(3-mercapto-propionyloxy)ethyl]isocyanurate (TEMPIC); dipentaerythritol hexa(3-mercapto-propionate) (Di-PETMP); ethoxylated trimethylolpropane tri(3-mercapto-propionate) (ETTMP); polycaprolactone tetra(3-mercapto-propionate) (PCL4MP); pentaerythritol tetramercaptoacetate (PETMA); trimethylol-propane trimercaptoacetate (TMPMA); or glycol dimercaptoacetate (GDMA).

In one embodiment, the at least one urease source is a watermelon seed. In one embodiment, the watermelon seed is a ground watermelon seed. In one embodiment, the ground watermelon seed has a particle size of about 425 μm or less.

In one embodiment, the concentration of the polyhydroxy monomer, the borate ion source, the epoxy resin, the compound comprising one or more thiol groups, the urea and the urease source are each independently selected to control the rate of polymerization.

The invention also provides a method for temporal control of the induction time in a polymerization reaction. In one embodiment, the method comprises (1) providing a first composition comprising: polyhydroxy monomer, and a borate ion source; or an epoxy resin, and a compound comprising one or more thiol groups; (2) providing a second composition comprising urea and a urease source; and (3) mixing the first composition and the second composition. In one embodiment, the concentrations of one or more of the polyhydroxy monomers, the borate ion source, the compound comprising one or more thiol groups, the urea concentrations and urease source concentration are selected to temporally control induction time of the polymerization reaction.

In one embodiment, the polyhydroxy monomer is PVA. In one embodiment, the borate ion source is boric acid. In one embodiment, the epoxy resin is polyethylene glycol diglycidyl ether (PEGDGE). In one embodiment, the compound comprising one or more thiol groups is ethoxylated trimethylolpropane tri(3-mercapto-propionate) (ETTMP).

In one embodiment, wherein the at least one urease source is a watermelon seed. In one embodiment, the watermelon seed is a ground watermelon seed. In one embodiment, the ground watermelon seed has a particle size of about 425 μm or less.

In one embodiment, the ratio of the urea concentration to the at least one urease source concentration is about 3:100, about 1:30, about 3:70, about 1:20, about 3:50, about 3:40, about 3:30, about 3:20, or about 3:10.

In one embodiment, the at least one urease source is a ground watermelon seed, and the concentration of the urease is increased by decreasing the particle size of the ground watermelon seed.

BRIEF DESCRIPTION OF THE DRAWINGS

The following detailed description of preferred embodiments of the invention will be better understood when read in conjunction with the appended drawings. For the purpose of illustrating the invention, there are shown in the drawings embodiments which are presently preferred. It should be understood, however, that the invention is not limited to the precise arrangements and instrumentalities of the embodiments shown in the drawings.

DETAILED DESCRIPTION

Figure 1:
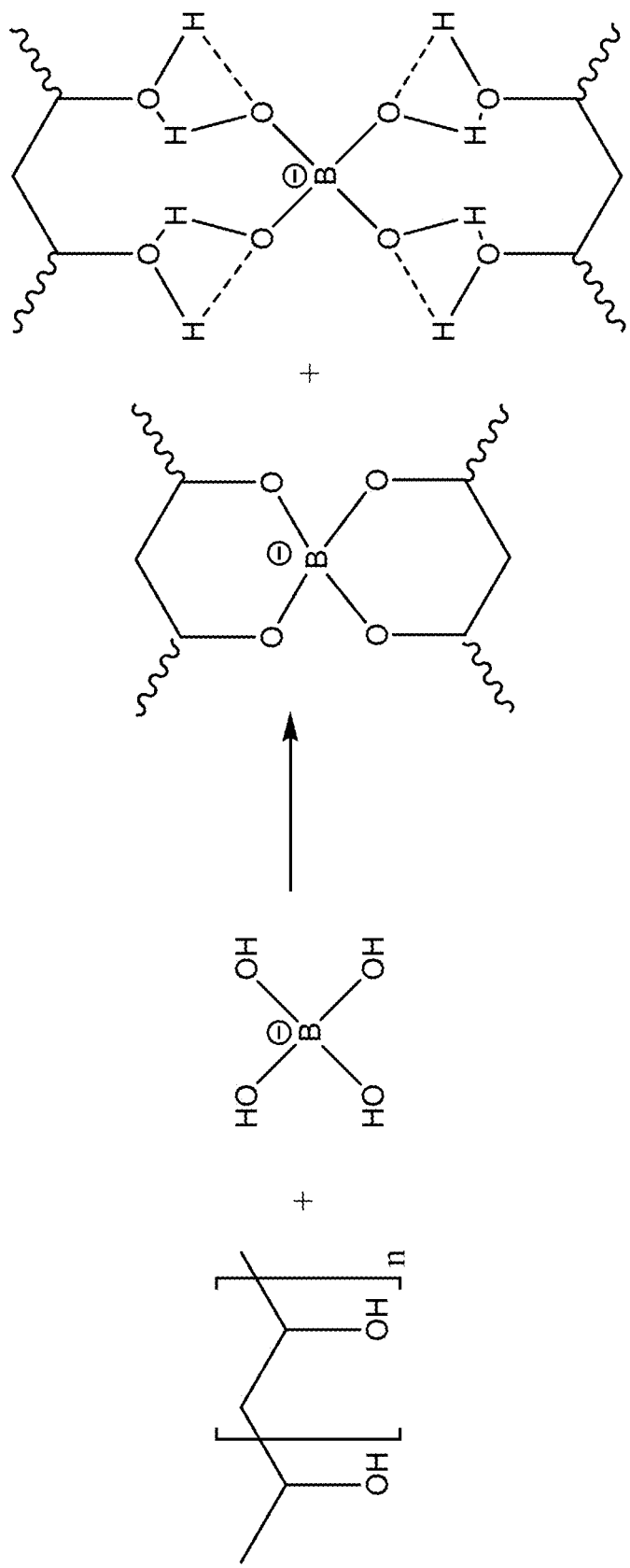
FIG. 1 depicts the resulting crosslink in the polymer produced from the crosslinking of PVA and borate.

The present invention is based, in part, on the unexpected finding that the rate of polymerization of a polyhydroxy monomer and borate can be controlled through a urea-urease reaction. As described herein, boric acid in water is in equilibrium with the borate anion, this equilibrium strongly favors the formation of acid and is, therefore, not enough to produce a crosslinked gel on its own with PVA. To shift the equilibrium to borate, enzymatic hydrolysis of urea is exploited. The combination of urea and ground watermelon seeds, where the watermelon seeds, which have high amounts of urease, will catalyze the hydrolysis of urea to form ammonia and carbon dioxide. Thus, the addition of urea and watermelon seeds to the polyhydroxy monomer and borate solution increases the pH, driving the polymerization of the polyhydroxy monomer and borate.

The invention further relates to the discovery that the induction time of the polymerization reaction of the polyhydroxy monomer and borate may be finely tuned. The enzymatic hydrolysis of urea is a "clock reaction," meaning the production of ammonia is slow and gradual if the pH of solution is less than 7.4, until the concentration is high enough for a catalytic effect that produces larger amounts of ammonia and raises the pH to 9. Thus, it is described herein that it is possible to generate a polyhydroxy monomer and borate mixture (for example, PVA and boric acid) that remains substantially unpolymerized for a programmed period of time, so that the monomer mixture may be handled as a malleable liquid for the programmed period of time for processing like coating, casting and molding, followed by rapid crosslinking polymerization.

The present invention includes novel polymerization compositions and kits. In one embodiment, the composition comprises a polyhydroxy monomer, and a borate ion source. In one embodiment, the composition further comprises urea and at least one urease source. In one embodiment, the crosslinking of the monomeric units may be temporally controlled.

The present invention also includes novel methods of controlling the rate of polymerization. In one embodiment, the methods comprise selecting a urease concentration, where in the urease concentration temporally controls the rate of polymerization.

Definitions

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are described.

As used herein, each of the following terms has the meaning associated with it in this section.

The articles "a" and "an" are used herein to refer to one or to more than one (i.e., to at least one) of the grammatical object of the article. By way of example, "an element" means one element or more than one element.

"About" as used herein when referring to a measurable value such as an amount, a temporal duration, and the like, is meant to encompass variations of ±20% or ±10%, more preferably ±5%, even more preferably ±1%, and still more preferably ±0.1% from the specified value, as such variations are appropriate to perform the disclosed methods.

The terms "first," "second," and the like, herein do not denote any order, quantity, or importance, but rather are used to denote one element from another.

The term "monomer" refers to any discreet chemical compound of any molecular weight.

As used herein, the term "polymer" refers to a molecule composed of repeating structural units typically connected by covalent chemical bonds. The term "polymer" is also meant to include the terms copolymer and oligomers. In one embodiment, a polymer comprises a backbone (i.e., the chemical connectivity that defines the central chain of the polymer, including chemical linkages among the various polymerized monomeric units) and a side chain (i.e., the chemical connectivity that extends away from the backbone).

As used herein, the term "epoxy resin" refers to compounds which contain epoxide groups.

As used herein, the term "polymerization" or "crosslinking" refers to at least one reaction that consumes at least one functional group in a monomeric molecule (or monomer), oligomeric molecule (or oligomer) or polymeric molecule (or polymer), to create at least one chemical linkage between at least two distinct molecules (e.g., intermolecular bond), at least one chemical linkage within the same molecule (e.g., intramolecular bond), or any combinations thereof. A polymerization or crosslinking reaction may consume between about 0% and about 100% of the at least one functional group available in the system. In one embodiment, polymerization or crosslinking of at least one functional group results in about 100% consumption of the at least one functional group. In another embodiment, polymerization or crosslinking of at least one functional group results in less than about 100% consumption of the at least one functional group.

As used herein, the term "curable" as applied to a material refers to a material comprising at least one functional group that may undergo polymerization. The curable material may be non-polymerized (i.e., non-cured material), or may be submitted to polymerization conditions (such as chemical reagents or physical conditions) that induce polymerization of at least a fraction of the at least one polymerizable functional group (i.e., partially or fully cured material). In one embodiment, polymerization or crosslinking of the curable material results in about 100% consumption of the at least one functional group (i.e., fully cured). In another embodiment, polymerization or crosslinking of the curable material results in less than about 100% consumption of the at least one functional group (i.e., partially cured).

As used herein, the term "reaction condition" refers to a physical treatment, chemical reagent, or combination thereof, which is required or optionally required to promote a reaction. Non-limiting examples of reaction conditions are electromagnetic radiation, heat, a catalyst, a chemical reagent (such as, but not limited to, an acid, base, electrophile or nucleophile), and a buffer.

The term "desiccant" is used herein with reference to a sorbent, in the form of a solid, liquid, or gel which has an affinity for water, and absorbs or adsorbs moisture from it's surrounding, thus controlling the moisture in the immediate environment.

As used herein, the term "instructional material" includes a publication, a recording, a diagram, or any other medium of expression that may be used to communicate the usefulness of the compositions of the invention. In some instances, the instructional material may be part of a kit useful for generating a shape memory polymer system. The instructional material of the kit may, for example, be affixed to a container that contains the compositions of the invention or be shipped together with a container that contains the compositions. Alternatively, the instructional material may be shipped separately from the container with the intention that the recipient uses the instructional material and the compositions cooperatively. For example, the instructional material is for use of a kit; instructions for use of the compositions; or instructions for use of a formulation of the compositions.

Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

Compositions

The invention provides compositions comprising a polyhydroxy monomer, and a borate ion source. In one embodiment, the composition further comprises urea and at least one urease source.

In one embodiment, the polyhydroxy monomer includes, but is not limited to, poly(vinyl) alcohol (PVA), 1,4-butanediol, 1,6-hexanediol, ethylene glycol, 2-ethyl-1,3-hexanediol (EHD), 2-butyl-2-ethyl-1,3-propanediol (BEPG), 2,2,4-trimethyl-1,3-pentanediol (TMPD), 2,4-deithyl-1,5-pentanediol (PD-9), hydroquinone dihydroxyethyl ether (HQEE), diethylene glycol, guar gum, propylene glycol, trimethylolpropane, and glycerol. In one embodiment, the polyhydroxy monomer is PVA.

In one embodiment, the borate ion source includes, but is not limited to, boric acid, borax, calcium borate, sodium borate, sodium tetraborate, disodium tetraborate, and any combination there of.

The invention provides compositions comprising an epoxy resin, and a compound comprising one or more thiol groups. In one embodiment, the composition further comprises urea and at least one urease source.

In one embodiment, the epoxy resin includes, but is not limited to, ethylene glycol diglycidyl ether (EGDGE), n-butyl glycidyl ether (BGE), polypropylene glycol diglycidyl ether (PPGDGE), and polyethylene glycol diglycidyl ether (PEGDGE).

In one embodiment, the compound comprising one or more thiol groups, but is not limited to, pentaerythritol tetra(3-mercapto-propionate) (PETMP); trimethylol-propane tri(3-mercapto-propionate) (TMPMP); glycol di(3-mercapto-propionate) (GDMP); tris[25-(3-mercapto-propionyloxy)ethyl]isocyanurate (TEMPIC); dipentaerythritol hexa(3-mercapto-propionate) (Di-PETMP); ethoxylated trimethylolpropane tri(3-mercapto-propionate) (ETTMP); polycaprolactone tetra(3-mercapto-propionate) (PCL4MP); pentaerythritol tetramercaptoacetate (PETMA); trimethylolpropane trimercaptoacetate (TMPMA); or glycol dimercaptoacetate (GDMA).

The invention provides compositions comprising first composition comprising first component, and a second component, wherein the first and second component do not react at pH 4, but react at a pH above 6. In one embodiment, the composition further comprises urea and at least one urease source. In one embodiment, the first and second component are respectively a polyhydroxy monomer and a borate ion source. In one embodiment, the first and second component are respectively an epoxy resin and a compound comprising one or more thiol groups.

In one embodiment, the urease source is purified urease. In one embodiment, the urease source is a stable urease source. For example, in one embodiment, the urease source has enhanced stability as compared to purified urease. For example, in one embodiment, the purified urease is distributed in a polyhydric material. In one embodiment, the urease source is urease adsorbed onto inorganic surfaces. In one embodiment, the urease source is urease adsorbed onto hydroxyapatite, or silica. In one embodiment, the urease source is urease bond urease to polymeric particles. In one embodiment, the urease is crosslinked to nylon powder and to starch through glutaraldehyde. In one embodiment, the urease source is from a natural material or product. For example, in one embodiment, the urease source is watermelon seeds, jack bean plants, common peas, common squash seeds, colocynth seeds, or soy bean. In one embodiment, the urease source is watermelon seeds.

In one embodiment, the watermelon seeds are ground watermelon seeds. For example, in one embodiment, watermelon seeds are ground. In one embodiment, the watermelon seed husks are removed by, for example, sifting. In one embodiment, the particle size of the ground watermelon seeds is about 425 µm or less. For example, in one embodiment, the particle size of the ground watermelon seeds is about 425 µm, about 415 µm, about 405 µm, about 400 µm, about 390 µm, about 380 µm, about 370 µm, about 360 µm, about 350 µm, about 340 µm, about 330 µm, about 320 µm, about 310 µm, about 300 µm, about 290 µm, about 280 µm, about 270 µm, about 260 µm, about 250 µm, about 240 µm, about 230 µm, about 220 µm, about 210 µm, about 200 µm, about 190 µm, about 180 µm, about 170 µm, about 160 µm, about 150 µm, about 140 µm, about 130 µm, about 120 µm, about 110 µm, or about 100 µm or less.

In one embodiment, the urea is purified urea.

In one embodiment, the composition comprises a filler. In one embodiment, the filler increases the viscosity of the composition. For example, in one embodiment the composition comprises fumed silica. In one embodiment, the filler is a solid filler. In one embodiment, the filler is not affected by pH change. For example, in on embodiment, the filler is kaolin clay, or bentonite clay.

In one embodiment, the concentration of each of the polyhydroxy monomer, the borate ion source, the urea and the urease source can be each independently selected to control the rate of polymerization.

In one embodiment, the ratio of polyhydroxy monomer:borate ion source is about 1:1, to about 20:1. In one embodiment, the ratio of polyhydroxy monomer:borate ion source is about 1:1, about 2:1, about 3:1, about 4:1, about 5:1, about 6:1, about 7:1, about 8:1, about 9:1, about 10:1, about 11:1, about 12:1, about 13:1, about 14:1, about 15:1, about 16:1, about 17:1, about 18:1, about 19:1, or about 20:1. For example, in one embodiment, the ratio of polyhydroxy monomer:borate ion source is about 1:10, about 1:12, about 1:20, or about 1:24.

In one embodiment, the ratio of compound comprising one or more thiol groups:epoxy resin is about 1:1, to about 20:1. In one embodiment, the ratio of compound comprising one or more thiol groups:epoxy resin is about 1:1, about 2:1, about 3:2, about 3:1, about 4:1, about 5:1, about 6:1, about 7:1, about 8:1, about 9:1, about 10:1, about 11:1, about 12:1, about 13:1, about 14:1, about 15:1, about 16:1, about 17:1, about 18:1, about 19:1, or about 20:1. For example, in one embodiment, the ratio of compound comprising one or more thiol groups:epoxy resin is about 1:1, about 2:1, about 3:2, or about 3:1.

In one embodiment, the urea:urease ratios are about 3:100 to about 3:10. For example, in one embodiment, the urea:urease ratios are about 3:100, about 1:30, about 3:70, about 1:20, about 3:50, about 3:40, about 3:30, about 3:20, or about 3:10.

In one embodiment, the composition comprises about 1% to about 20% of the polyhydroxy monomer. For example, in one embodiment, the composition comprises about 1%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, or about 20% of the polyhydroxy monomer.

In one embodiment, the composition comprises about 0.1% to about 2% of the borate ion source. For example, in one embodiment, the composition comprises about 0.10%, about 0.15%, about 0.20%, about 0.25%, about 0.30%, about 0.35%, about 0.40%, about 0.45%, about 0.50%, about 0.55%, about 0.60%, about 0.65%, about 0.70%, about 0.75%, about 0.80%, about 0.85%, about 0.90%, about 0.95%, about 1.00%, about 1.05%, about 1.10%, about 1.15%, about 1.20%, about 1.25%, about 1.30%, about 1.35%, about 1.40%, about 1.45%, about 1.50%, about 1.55%, about 1.60%, about 1.65%, about 1.70%, about 1.75%, about 1.80%, about 1.85%, about 1.90%, about 1.95%, or about 2.00% of the borate ion source. In one embodiment, the composition comprises about 0.40% of the borate ion source. In one embodiment, the composition comprises about 0.80% of the borate ion source.

In one embodiment, the composition comprises about 10 mM to about 100 mM urea. For example, in one embodiment, the composition comprises about 10 mM, about 15 mM, about 20 mM, about 25 mM, about 30 mM, about 35 mM, about 40 mM, about 45 mM, about 50 mM, about 55 mM, about 60 mM, about 65 mM, about 70 mM, about 75 mM, about 80 mM, about 85 mM, about 90 mM, about 95 mM, or about 100 mM urease. In one embodiment, the composition comprises about 50 mM urea.

In one embodiment, the composition comprises about 0.01% (w/v) to about 20% (w/v) of the urease source. For example, in one embodiment, the composition comprises about 0.01% (w/v), about 0.05% (w/v), about 0.10% (w/v), about 0.15% (w/v), about 0.20% (w/v), about 0.25% (w/v), about 0.30% (w/v), about 0.35% (w/v), about 0.40% (w/v), about 0.45% (w/v), about 0.50% (w/v), about 0.55% (w/v), about 0.60% (w/v), about 0.65% (w/v), about 0.70% (w/v), about 0.75% (w/v), about 0.80% (w/v), about 0.85% (w/v), about 0.90% (w/v), about 0.95% (w/v), about 1.0% (w/v), about 1.5% (w/v), about 2.0% (w/v), about 2.5% (w/v), about 3.0% (w/v), about 3.5% (w/v), about 4.0% (w/v), about 4.5% (w/v), about 5.0% (w/v), about 5.5% (w/v), about 6.0% (w/v), about 6.5% (w/v), about 7.0% (w/v), about 7.5% (w/v), about 8.0% (w/v), about 8.5% (w/v), about 9.0% (w/v), about 9.5% (w/v), about 10.0% (w/v), about 10.5% (w/v), about 11.0% (w/v), about 12.0% (w/v), about 13.0% (w/v), about 14.0% (w/v), about 15.0% (w/v), about 16.0% (w/v), about 17.0% (w/v), about 18.0% (w/v), about 19.0% (w/v), or about 20.0% (w/v), of the urease source.

In one embodiment, the concentration of urease is controlled by the particle size of the ground watermelon seed. For example, in one embodiment a small particle size results in an increased urease concentration. In one embodiment, a large particle size results in a decreased urease concentration. In some embodiments, the particle size of the ground watermelon is selected to control the rate of polymerization. In one embodiment, smaller particle size results in faster polymerization. In one embodiment, a large particle size results in slower polymerization.

In one embodiment, the activity of urease is controlled by the particle size of the ground watermelon seed. For example, in one embodiment a small particle size results in an increased urease activity. In one embodiment, a large particle size results in a decreased urease activity. In some embodiments, the particle size of the ground watermelon is selected to control the rate of polymerization. In one embodiment, smaller particle size results in faster polymerization. In one embodiment, a large particle size results in slower polymerization.

Methods

In one aspect, the invention provides a method for temporal control of the induction time in a polymerization reaction. In one embodiment, the method comprises providing a first composition comprising polyhydroxy monomer, and a borate ion source; providing a second composition comprising urea and a urease source; and mixing the first composition and the second composition, wherein the concentrations of one or more of the polyhydroxy monomer, the borate ion source, the urea and urease source are selected as to temporally control induction time of the polymerization reaction.

In one embodiment, the method comprises providing a first composition comprising an epoxy resin, and a compound comprising one or more thiol groups; providing a second composition comprising urea and a urease source; and mixing the first composition and the second composition, wherein the concentrations of one or more of the epoxy resin, compound comprising one or more thiol groups, the urea and urease source are selected as to temporally control induction time of the polymerization reaction.

In one embodiment, the epoxy resin is a water-soluble epoxy resin. In one embodiment, the epoxy resin includes, but is not limited to, ethylene glycol diglycidyl ether (EGDGE), n-butyl glycidyl ether (BGE), polypropylene glycol diglycidyl ether (PPGDGE), and polyethylene glycol diglycidyl ether (PEGDGE).

In one embodiment, the water-soluble epoxy resin is PEGDGE.

In one embodiment, the compound comprising one or more thiol groups comprises 2 thiol groups, 3 thiol groups, 4 thiol groups, 5 thiol groups, 6 thiol groups, 7 thiol groups, or 8 or more thiol groups.

In one embodiment, the compound comprising one or more thiol groups, but is not limited to, pentaerythritol tetra(3-mercapto-propionate) (PETMP); trimethylol-propane tri(3-mercapto-propionate) (TMPMP); glycol di(3-mercapto-propionate) (GDMP); tris[25-(3-mercapto-propionyloxy)ethyl]isocyanurate (TEMPIC); dipentaerythritol hexa(3-mercapto-propionate) (Di-PETMP); ethoxylated trimethylolpropane tri(3-mercapto-propionate) (ETTMP); polycaprolactone tetra(3-mercapto-propionate) (PCL4MP); pentaerythritol tetramercaptoacetate (PETMA); trimethylol-propane trimercaptoacetate (TMPMA); or glycol dimercaptoacetate (GDMA).

In one embodiment, the compound comprising one or more thiol groups is ETTMP.

In one embodiment, the method comprises providing a first composition comprising first component, and a second component, wherein the first and second component do not react at pH 4, but react at a pH above 6; providing a second composition comprising urea and a urease source; and mixing the first composition and the second composition, wherein the concentrations of one or more of the epoxy resin, compound comprising one or more thiol groups, the urea and urease source are selected as to temporally control induction time of the polymerization reaction. In one embodiment, the first and second component are respectively a polyhydroxy monomer and a borate ion source. In one embodiment, the first and second component are respectively an epoxy resin and a compound comprising one or more thiol groups.

In one embodiment, to have a long induction time of the polymerization reaction, the concentration of the urease is low. In one embodiment, to short the induction time of the polymerization reaction, the concentration of the urease is high. In one embodiment, to have a long induction time of the polymerization reaction, the concentration of the urea is low. In one embodiment, to have a short induction time of the polymerization reaction, the concentration of the urea is high.

In one embodiment, to increase the induction time of the polymerization reaction, the concentration of the urease is decreased. In one embodiment, to decrease the induction time of the polymerization reaction, the concentration of the urease is increased. In one embodiment, to increase the induction time of the polymerization reaction, the concentration of the urea is decreased. In one embodiment, to decrease the induction time of the polymerization reaction, the concentration of the urea is increased.

In one embodiment, induction time of polymerization is about 30 minutes to about 3 hours. In one embodiment, when the induction time of polymerization are about 30 minutes to about 3 hours, the concentration of the urease source is high. For example, in one embodiment, when the induction time of polymerization are about 30 minutes to about 3 hours, the concentration of the urease source is about 10%.

In one embodiment, induction time of polymerization is about 8 hours to 48 hours. In one embodiment, when the induction time of polymerization are about 8 hours to 48 hours, the concentration of the urease source is low. For example, in one embodiment, when the induction time of polymerization are about 8 hours to 48 hours, the concentration of the urease source is about 0.50% to about 5%.

In one embodiment, the urea:urease ratios include, but are not limited to about 1:30, about 1:20, about 3:10, about 3:20, about 3:40, about 3:50, about 3:70 and about 3:100.

In one embodiment, the urease source is watermelon seed or watermelon seed particles. In one embodiment, the concentration of the urease is modulated by altering the size of the watermelon seed particles. For example, in one embodiment, the watermelon particle size is decreased to increase particle size. In one embodiment, the watermelon particle size is increased to decrease particle size.

In one embodiment, the induction time in a polymerization reaction can be tuned to be about 10 minutes to about 3 hours. For example, in one embodiment, the induction time in a polymerization reaction can be tuned to be about 10 minutes, about 20 minutes, about 30 minutes, about 40 minutes, about 50 minutes, about 60 minutes, about 70 minutes, about 80 minutes, about 90 minutes, about 100 minutes, about 110 minutes, about 120 minutes, about 130 minutes, about 140 minutes, about 150 minutes, about 160 minutes, about 170 minutes, or about 180 minutes.

In one aspect, the invention provides a method for generating a polymeric material. In one embodiment, the method comprises providing a first composition comprising polyhydroxy monomer, and a borate ion source; providing a second composition comprising urea and a urease source; and mixing the first composition and the second composition, wherein the concentrations of the urea and urease source are selected as to provide a specific induction time for the polymerization reaction of the composition; shaping the composition to a desired form or shape within the specific induction time; and, allowing the composition to undergo polymerization, thereby generating the polymeric material.

In one embodiment, the polymeric material is an adhesive material. In one embodiment, the composition is an aqueous composition.

In one embodiment, the urease hydrolyzes urea to form ammonia and carbon dioxide. In one embodiment, the hydrolysis of urea increases the pH of the composition, thereby inducing the polymerization of the polyhydroxy monomer with the borate ion.

The invention also provides a method of isolating a urea source. In one embodiment the method comprises (1) milling a watermelon seed; (2) forming a mixture comprising the milled watermelon seed and acetone; (3) isolating a supernatant from the mixture; (4) decant the supernatant using a filter; and (5) evaporating the acetone to provide an isolated a urea source.

In one embodiment, milling the watermelon seed comprises milling at 25,000 rpm. In one embodiment, milling the watermelon seed comprises milling for about 1 to about 2 minutes.

In one embodiment, the mixture comprising the milled watermelon seed and acetone comprises milled watermelon seed:acetone ratio of 5:1 (w/w).

In one embodiment, the method further comprises incubating the mixture. In one embodiment, the mixture is incubated for a sufficient time to allow sedimentation.

In one embodiment, decanting the supernatant using a filter comprising decanting the supernatant using a #1 Whatman filter.

In one embodiment, the method further comprises washing the supernatant with acetone.

In one embodiment, evaporating the acetone to provide an isolated a urea source comprises incubating at room temperature for about 4 hours to about 18 hours. In one embodiment, evaporating the acetone to provide an isolated a urea source comprises incubating at room temperature for about 8 hours to about 12 hours.

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. Any numerical value, however, inherently contain certain errors necessarily resulting from the standard deviation found in their respective testing measurements.

Those skilled in the art will recognize, or be able to ascertain using no more than routine experimentation, numerous equivalents to the specific procedures, embodiments, claims, and examples described herein. Such equivalents were considered to be within the scope of this invention and covered by the claims appended hereto. For example, it should be understood, that modifications in reaction conditions, including but not limited to reaction times, reaction size/volume, and experimental reagents, such as solvents, catalysts, pressures, atmospheric conditions, e.g., nitrogen atmosphere, and reducing/oxidizing agents, with art-recognized alternatives and using no more than routine experimentation, are within the scope of the present application.

Kits

The present invention provides kits that can be used in any of the methods described herein. For example, the invention provides kits for forming a polymeric material. In one embodiment, the kit allows for the induction of the formation of the polymeric material to be temporally controlled.

In one embodiment, the kit comprises a polyhydroxy monomer, a borate ion source, urea, and a urease source. The polyhydroxy monomer, borate ion source, urea, and a urease source can be contained in individual containers or in a single container. In one embodiment, the polyhydroxy monomer, and borate ion source are contained in a single container. In one embodiment, the urea and urease source are contained in a single container. In one embodiment, the urea, and urease source are contained in separate containers.

For example, in one embodiment, the kit comprises first container comprising a first composition comprising a polyhydroxy monomer, and a borate ion source, and a second container comprising a second composition comprising a urea. In one embodiment, the second composition further comprises a urease source. In one embodiment, the kit further comprises a third container comprising third composition comprising a urease source. In one embodiment, the containers are glass or plastic. In one embodiment, the kit comprises a plurality of containers each comprising one or more of a polyhydroxy monomer, a borate ion source, urea and a urease source.

In one embodiment, the kit comprises an epoxy resin, a compound comprising one or more thiol groups, urea, and a urease source. The epoxy resin, compound comprising one or more thiol groups, and a urease source can be contained in individual containers or in a single container. In one embodiment, the epoxy resin, compound comprising one or more thiol groups are contained in a single container. In one embodiment, the urea and urease source are contained in a single container. In one embodiment, the urea, and urease source are contained in separate containers.

For example, in one embodiment, the kit comprises first container comprising a first composition comprising an epoxy resin, and a compound comprising one or more thiol groups, and a second container comprising a second composition comprising a urea. In one embodiment, the second composition further comprises a urease source. In one embodiment, the kit further comprises a third container comprising third composition comprising a urease source. In one embodiment, the containers are glass or plastic. In one embodiment, the kit comprises a plurality of containers each comprising one or more of an epoxy resin, a compound comprising one or more thiol groups, urea, and a urease source.

In one embodiment, the kit comprises an epoxy resin, a compound comprising one or more thiol groups, urea, and a urease source. The epoxy resin, compound comprising one or more thiol groups, and a urease source can be contained in individual containers or in a single container. In one embodiment, the epoxy resin, compound comprising one or more thiol groups are contained in a single container. In one embodiment, the urea and urease source are contained in a single container. In one embodiment, the urea, and urease source are contained in separate containers.

For example, in one embodiment, the kit comprises first container comprising a first composition comprising an epoxy resin, and a compound comprising one or more thiol groups, and a second container comprising a second composition comprising a urea. In one embodiment, the second composition further comprises a urease source. In one embodiment, the kit further comprises a third container comprising third composition comprising a urease source. In one embodiment, the containers are glass or plastic. In one embodiment, the kit comprises a plurality of containers each comprising one or more of an epoxy resin, a compound comprising one or more thiol groups, urea, and a urease source.

In one embodiment, the kit comprises a first component, a second component, urea, and a urease source, wherein the first and second component do not react at pH 4, but react at a pH above 6. The first component, second component, and a urease source can be contained in individual containers or in a single container. In one embodiment, the first component, and second component are contained in a single container. In one embodiment, the urea and urease source are contained in a single container. In one embodiment, the urea, and urease source are contained in separate containers.

For example, in one embodiment, the kit comprises first container comprising a first composition comprising a first component and second component, and a second container comprising a second composition comprising a urea. In one embodiment, the second composition further comprises a urease source. In one embodiment, the kit further comprises a third container comprising third composition comprising a urease source. In one embodiment, the containers are glass or plastic. In one embodiment, the kit comprises a plurality of containers each comprising one or more of a first component, second component, urea, and a urease source.

In one embodiment, the first composition is an aqueous solution, or a powder. In one embodiment, the first composition has a pH of less than about 7.4.

In one embodiment, the second container further comprises a urea and a urease source. In one embodiment, the urease source is a natural material or natural product. In one embodiment, the urease source is watermelon seeds. In one embodiment, the watermelon seeds are ground.

In one embodiment, the second container is void of moisture. In one embodiment, the second container is vacuum sealed. In one embodiment, the second container further comprises a desiccant. For example, the desiccant can include, but is not limited to, activated alumina, aerogel, benzophenone, bentonite clay, calcium chloride, calcium oxide, calcium sulfate (Drierite), cobalt(II) chloride, copper (II) sulfate, lithium chloride, lithium bromide, magnesium sulfate, magnesium perchlorate, molecular sieve, potassium carbonate, potassium hydroxide, silica gel, sodium, sodium chlorate, sodium chloride, sodium hydroxide, sodium sulfate, sucrose. In one embodiment, the desiccant is fumed silica. In one embodiment, the desiccant prevents the urease from substantially hydrolyzing the urea to form ammonia and carbon dioxide.

In one embodiment, the kit further comprises an instruction material. In one embodiment, the instructional material comprises instructions for forming a polymeric adhesive.

EXPERIMENTAL EXAMPLES

The invention is further described in detail by reference to the following experimental examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided herein.

Without further description, it is believed that one of ordinary skill in the art can, using the preceding description and the following illustrative examples, make and utilize the compounds of the present invention and practice the claimed methods. The following working examples therefore, specifically point out the preferred embodiments of the present invention, and are not to be construed as limiting in any way the remainder of the disclosure.

Example 1: Time-Lapse Enzymatic Hydrolysis for Poly(Vinyl) Alcohol and Boric Acid Adhesive The addition of a polyhydroxy monomer to a borate anion source, such as borax, is known to form a crosslinked gel commonly referred to as Slime. Described herein is an adhesive based on this principle, in which poly(vinyl) alcohol (PVA) is crosslinked by the borate ion from aqueous boric acid to form a polymer with high hydrogen bonding capabilities for adhesion (FIG. 1).

Figure 2:
FIG. 2 depicts the equilibrium reaction of boric acid dissolved in water.
Figure 2:
Figure 2:
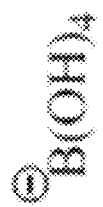
Figure 2:
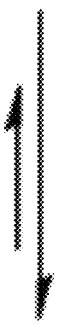
Figure 2:
Figure 2:
Figure 2:
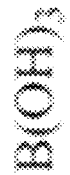

Although boric acid in water is in equilibrium with the borate anion, this equilibrium strongly favors the formation of acid and is, therefore, not enough to produce a crosslinked gel on its own with PVA (FIG. 2).

Figure 3:
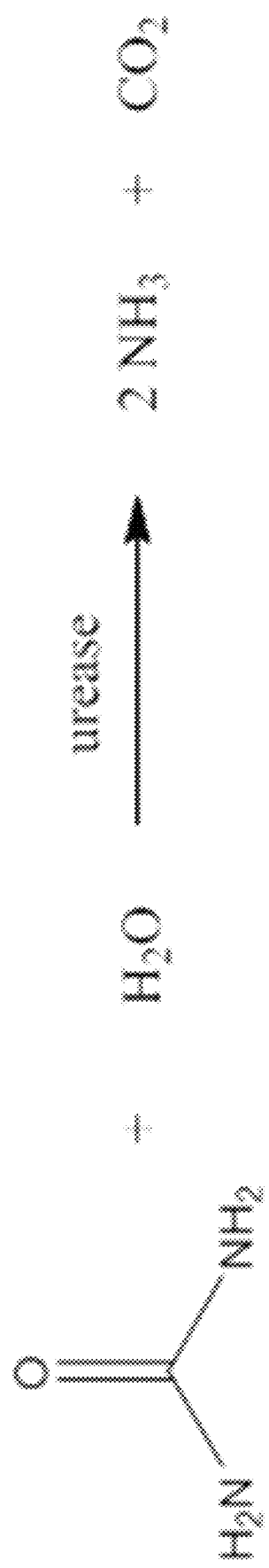
FIG. 3 depicts the enzymatic hydrolysis of urea that ultimately forms ammonia and carbon dioxide.

However, the addition of a base shifts this equilibrium toward borate, which will react with PVA to produce the adhesive polymer. This base addition is achieved naturally by combining urea and watermelon seeds with the monomer solution, where the watermelon seeds, which have high amounts of the enzyme urease, will hydrolyze the urea to form ammonia and carbon dioxide (FIG. 3).

This production of ammonia will raise the pH of the solution, making the solution basic enough to form more borate anion and crosslink the PVA network. The enzymatic hydrolysis of urea is a clock reaction, meaning the production of ammonia is slow and gradual if the reaction conditions are anything but optimal for the enzyme, in this case if the pH of solution is less than 7.4, until the concentration is high enough for a catalytic effect that produces larger amounts of ammonia and raises the pH. For example, the ammonia and can raise the pH to 9. Boric acid has a lower pH closer to 5, causing an induction period before significant amounts of ammonia are produced by hydrolysis, therefore allowing the time required for polymerization to be tuned by altering concentrations of urea and watermelon seeds, as well as boric acid concentration to some extent.

Figure 4:
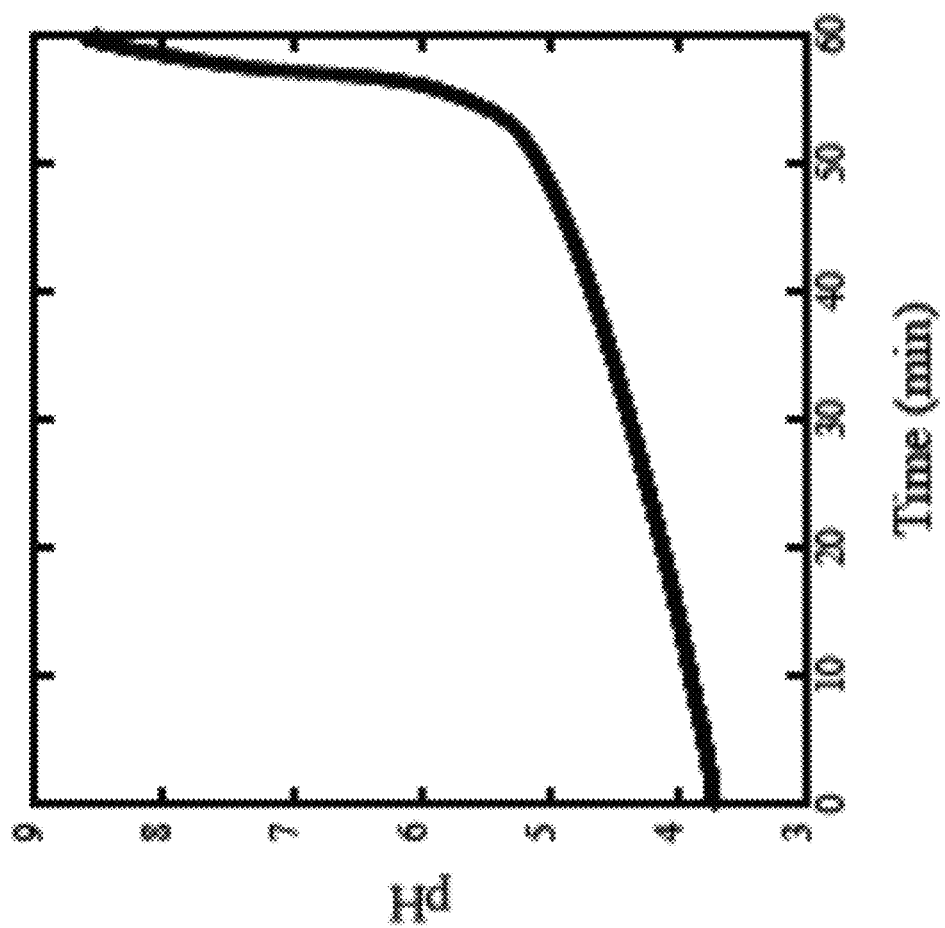
FIG. 4 depicts the rate-pH curve for urea-urease reaction.

The rate-pH curve for urea-urease reaction is plotted in FIG. 4. Base-catalyzed feedback and a pH clock are observed in this reaction by adjusting the initial pH to about 4. Because the reaction produces base (through ammonia), the rate accelerates as the reaction proceeds, reaching a maximum at pH of 7.

Initial Polymerization/Adhesive Results

Successful trials have been conducted using 4% PVA (98-99% hydrolyzed) and 4% boric acid in a 10:1 ratio. Previous formulations included replacing PVA monomer with guar gum and replacing boric acid with borax. However, guar gum polymers produced clumpy, more brittle polymers when crosslinked, and monomers crosslinked with borax had no tunable time frame as the polymer immediately crosslinked to a brittle, harder polymer. These brittle polymers are probably the result of the borate ester crosslinking rather than the hydrogen bonded network of tetrahydroxyborate, which does not make for a good adhesive anyway. These monomers were polymerized using 50 mM urea with various amounts of ground and powdered watermelon seeds, including 200 mg, 400 mg, 1 g, and 2 g. By using different particle sizes—ground watermelon seeds or seeds with the husks sifted out to produce particles of 425 µm or less—the amount of urease was changed and, therefore, the gel time affected. The same can be said with the concentration of seeds introduced, with larger amounts causing a faster gelation time than lesser. From the concentrations tried, it is possible to have a gelation range of 30 minutes to several hours, and the adhesive is not limited to only these concentrations and time range.

The adhesive properties have been tested using small polystyrene blocks on wood planks and against painted drywall. The basic formulation tested contained 10:1 PVA: boric acid (4% solutions), 50 mM urea, and 200 mg ground watermelon seeds. Without filler in the system, the viscosity of the initial adhesive solution is similar to that of water. Regardless, when a thin layer was smeared on the polystyrene block and stuck to the wood plank, the ungelled polymer adhered the polystyrene to wood well enough to be immobile against gravity after 30 minutes, and after overnight curing the adhesive was strong enough to lift the wood plank using the polystyrene block. Though the enzymatic reaction produces volatile ammonia gas, the gas was not pungent enough to be noticeable from only a foot away from either the thin layered adhesive or the polymerized mother liquor. Similar results were observed by sticking polymerized, viscous gel to polystyrene and adhering it to drywall.

The adhesive system can be kept in two parts. The monomers mixed together in a large solution will not polymerize of their own accord, even after several months, and perform the same as a freshly made solution. The solid urea and watermelon seeds require the absence of moisture to prevent reaction in the solid state. This can be achieved by vacuum packing the solids, as well as adding desiccant/filler such as fumed silica, and the prevention has been observed to be effective for one month or more in a closed system. The watermelon seeds will decrease in activity over time due to enzyme degradation, though after three months the seeds were still effective but took twice the time for gelation.

Example 2: Watermelon Seeds Extraction Protocol

Figure 5:
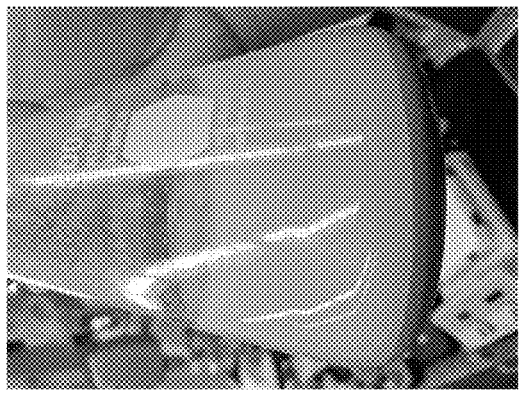
FIG. 5 demonstrates steps 1-9 of extracting urease with acetone from watermelon seeds.
Figure 5:
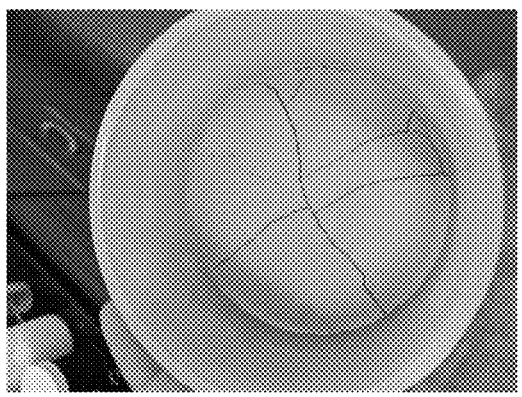
Figure 5:
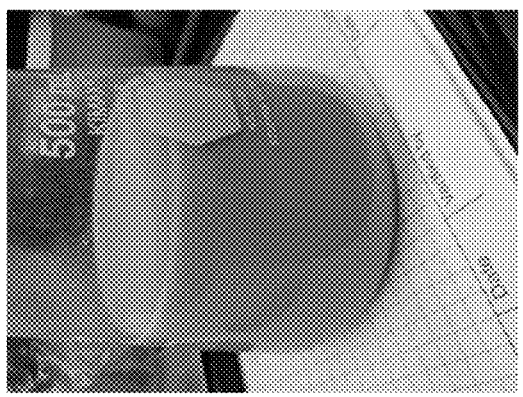
Figure 5:
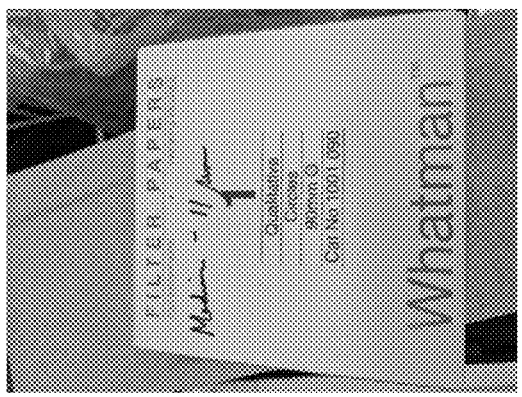
Figure 5:

The data presented herein demonstrates an inexpensive source of urease using ground watermelon seeds that are extracted with acetone:
1. Mill seeds @ 25 k rpm for 1-2 minutes
2. Scrape milled material into suitable flask
3. Add acetone as extraction solvent and swirl
4. Ratio of acetone to seeds is 5:1 w/w (we use 250 g Acetone to 50 g seeds)
5. Let the solution sediment, a noticeable tan colored supernatant will be our desired powder
6. The very last layer will be the seed husks and large particulates
7. Decant this tan solution with Büchner filtration using a #1 Whatman filter (11 μm, medium flow)
8. Wash with more acetone as needed to recover more fines
9. Let air dry overnight to evaporate acetone FIG. 5 demonstrates steps 1-9 of extracting urease with acetone from watermelon seeds.

Figure 6:
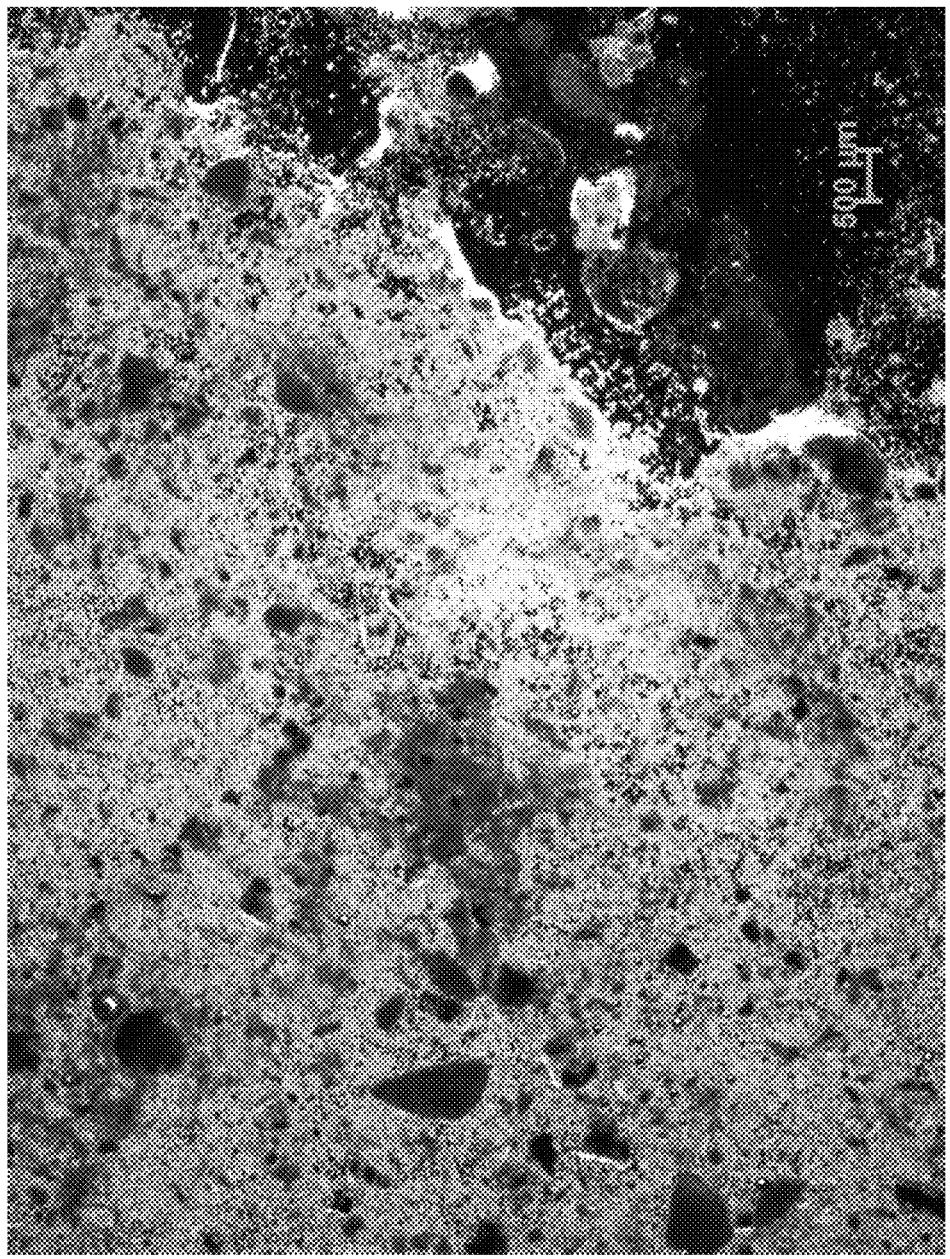
FIG. 6 depicts a picture of the seed mixture of husks and fines.

FIG. 6 depicts a picture of the seed mixture of husks and fines.

Figure 7:
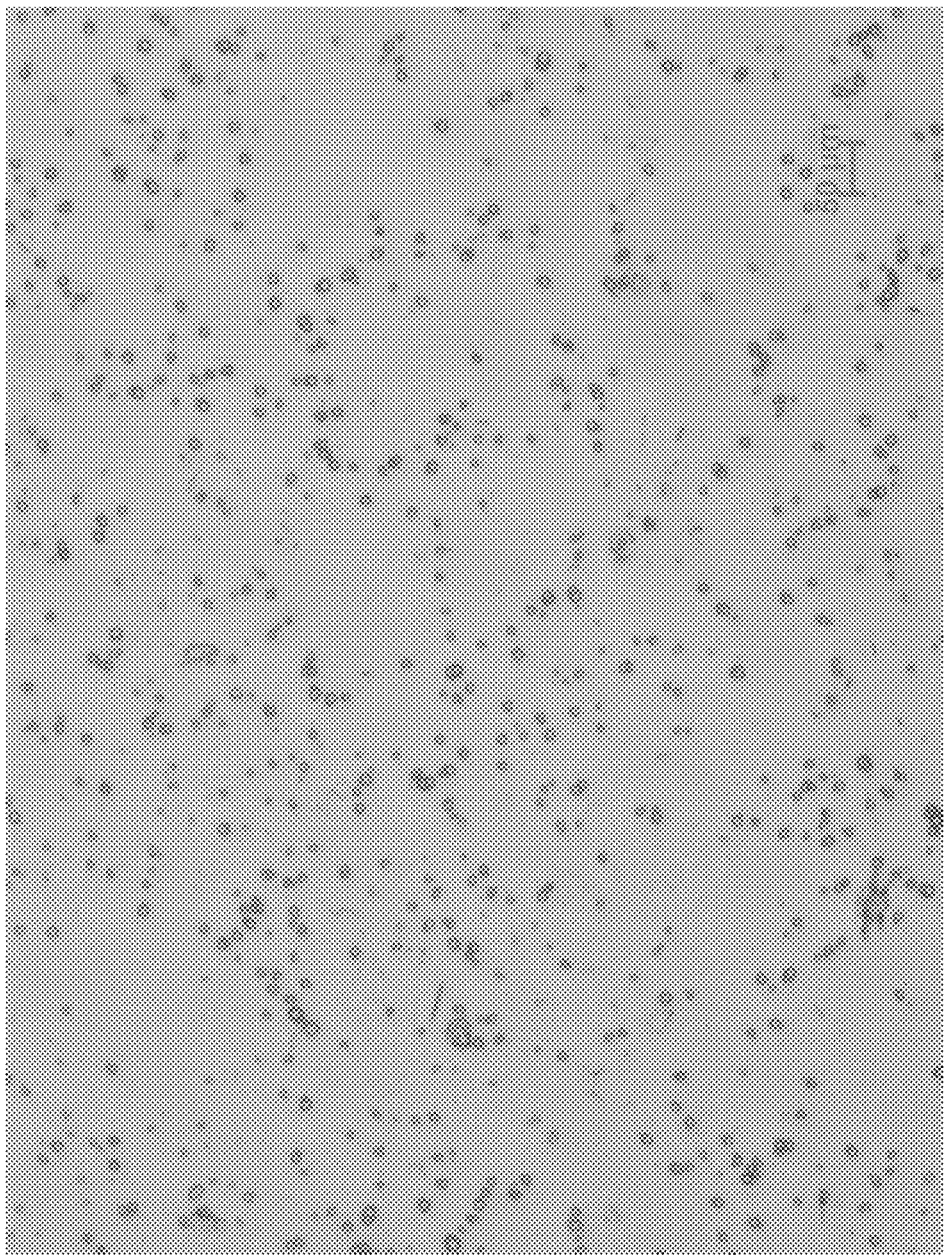
FIG. 7 depicts an image of the extracted powder.

FIG. 7 depicts an image of the extracted powder.

Example 3: Time-Lapse Enzymatic Hydrolysis for Trithiol and Epoxy

A water-soluble epoxy resin and water-soluble mutithiol compound are dissolved in an aqueous solution at pH 4 containing urea. The urease powder (from water melon seeds; see examples 1 and 2) is mixed. As the pH rises from the urea-urease reaction, the thiols become deprotonated and react with the epoxy. Any epoxy system with an amine can be cured in this manner as longer as the amount of amine is sufficiently low to avoid buffering the urea-urease reaction.

Figure 8:
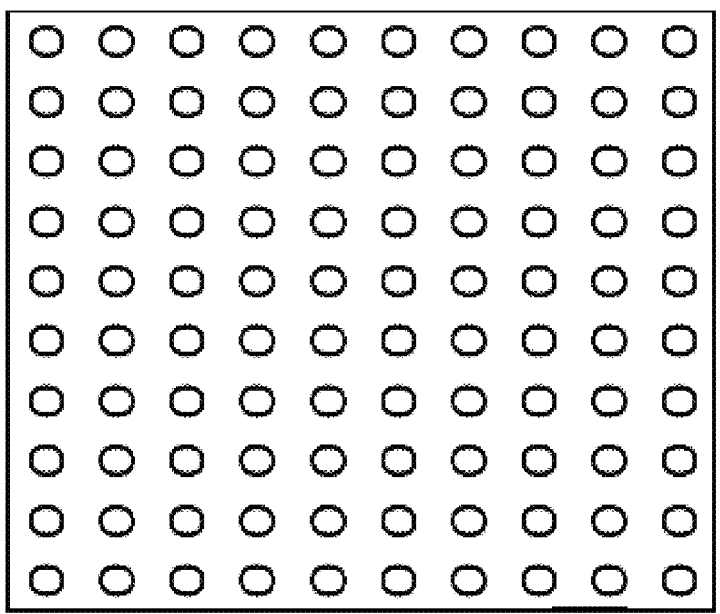
FIG. 8 depicts a schematic of on-demand thiol-epoxide polymerization. Thiol and epoxide monomers [m] are combined, monomers are aliquoted with aqueous solution (0.2 M urea) for varying concentrations, initiator [I] is added to reaction mixture and pipetted into mold for gelation.
Figure 8:
Figure 8:
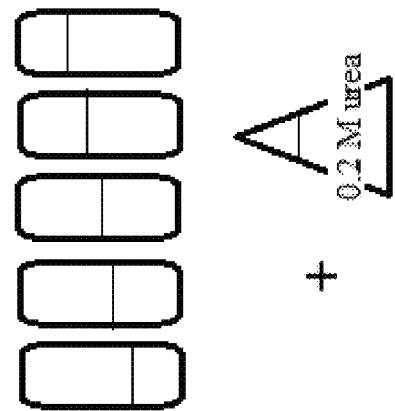
Figure 8:
Figure 8:
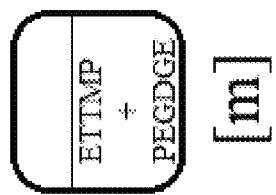

The data presented herein demonstrates an exemplary system using ETTMP and PEGDGE (FIG. 8).

Calculation of Hardener Content for Epoxy Resins:

$$\text{Thiocure (g)} = \text{epoxy value} \times \text{SH-equivalent}$$

PEGDGE 500 epoxy value: 264-209 epoxy equiv. wt. (bottle)÷1/100=0.345-0.379
ETTMP 1300 SH equivalent: 435-448 (SDS)
Thiocure (g)=150-170 phr; value used=154 phr $$\text{Monomer content } [m] = 1.54X + X, \text{ where } X = \text{epoxy wt. (g)}$$

Aqueous addition (wt %): 0.2 M urea in 100 mL DI water $$50\% \text{ aq: } 20\text{ g} = 10\text{ g } [m] + 10\text{ g aq}$$

Initiator concentration [I]:

$$WMS(g) = 0.25\text{ g } WMS \div 5\text{ g } 0.2\text{ M urea} = 5\% \text{ aqueous wt}$$

$$\text{NaOH}(0.1\text{ M}) = \max 5\text{ mg KOH/g SH(SDS acid number)} \rightarrow 0.8\text{ mL } 0.1\text{ M NaOH/g SH}$$

Polymerization: excess [m] and reaction solutions capped and stored on bench top; open mold stored in hood during gelation. After polymerization collect mold samples and store in capped vial.

WMS used are those extracted with acetone. Weight ratio is from previous adhesive formulation; the reaction time of WMS with 0.2 M urea will be studied in 4% PVA to find concentration that produces a "timely" reaction.

| | Formulation | | | | | |
|---|---|---|---|---|---|---|
| | [m] | | Aq | [I] | | WMS Reaction |
| Aq wt % | ETTMP 1300 | PEGDGE 500 | 0.2M urea | 0.1M NaOH | WMS | Bulk gelation | Mold Sample |
| 30% | 8.5 g | 5.5 g | 6 g | 6.8 mL | 0.3 g | Overnight; unreacted liquid layer | N.R. |
| 40% | 7.3 g | 4.7 g | 8 g | 5.8 mL | 0.4 g | Overnight | N.R. |
| 50% | 6.1 g | 3.9 g | 10 g | 4.9 mL | 0.5 g | Overnight | Overnight; visibly moist sticky |
| 60% | 4.9 g | 3.1 g | 12 g | 3.9 mL | 0.6 g | ≈3 hours | Overnight; sticky but firm |
| 70% | 3.6 g | 2.4 g | 14 g | 2.9 mL | 0.7 g | ≈3 hours; completely un-gelled overnight | ≈3 hours; half way un-gelled overnight |

These results show that 60% aq formed a firm sticky gel overnight, while 70% aq degraded overnight and 50% aq might not have reacted completely NaOH is used for initiation to compare mechanical and degradation properties with WMS samples. NH₄OH was used to initiate the reaction but none of the samples polymerized, likely due to the loss of ammonia over time (it was an old, opened bottle).

Interesting that 30-40% bulk samples that were capped gelled but neither reacted in the mold. Diffusion of ammonia again; samples that gelled overnight were sunken in on the top from evaporation. Therefore, an inverted bowl is placed over the mold with openings around the bottom to prevent excess evaporation caused by air flow and allow diffusion of ammonia outside of the container.

It was clear that 70% aq at this urea-WMS concentration produced too much ammonia, since both bulk and mold samples polymerized in about three hours and completely un-gelled in a little over 12 hours.

The disclosures of each and every patent, patent application, and publication cited herein are hereby incorporated herein by reference in their entirety. While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

The invention claimed is:

1. A composition for forming a polymer comprising a polyhydroxy monomer, and a borate ion source; or an epoxy resin and a compound comprising one or more thiol groups; and
wherein the composition further comprises urea and at least one urease source.

2. The composition of claim 1, wherein the polyhydroxy monomer is selected from the group consisting of poly(vinyl) alcohol (PVA), 1,4-butanediol, 1,6-hexanediol, ethylene glycol, 2-ethyl-1,3-hexanediol (EHD), 2-butyl-2-ethyl-1,3-propanediol (BEPG), 2,2,4-trimethyl-1,3-pentanediol (TMPD), 2,4-deithyl-1,5-pentanediol (PD-9), hydroquinone dihydroxyethyl ether (HQEE), diethylene, glycol, propylene glycol, trimethylolpropane, and glycerol.

3. The composition of claim 1, wherein the borate ion source is selected from the group consisting of boric acid, borax, calcium borate, sodium borate, sodium tetraborate, disodium tetraborate, and any combination thereof.

4. The composition of claim 1, wherein the epoxy resin is selected from the group consisting of ethylene glycol diglycidyl ether (EGDGE), n-butyl glycidyl ether (BGE), polypropylene glycol diglycidyl ether (PPGDGE), and polyethylene glycol diglycidyl ether (PEGDGE).

5. The composition of claim 1, wherein the compound comprising one or more thiol groups is selected from the group consisting of pentaerythritol tetra(3-mercapto-propionate) (PETMP); trimethylol-propane tri(3-mercapto-propionate) (TMPMP); glycol di(3-mercapto-propionate) (GDMP), tris[25-(3-mercapto-propionyloxy)ethyl]isocyanurate (TEMPIC); dipentaerythritol hexa(3-mercapto-propionate) (Di-PETMP); ethoxylated trimethylolpropane tri(3-mercapto-propionate) (ETTMP); polycaprolactone tetra(3-mercapto-propionate) (PCL4MP); pentaerythritol tetramercaptoacetate (PETMA); trimethylol-propane trimercaptoacetate (TMPMA); or glycol diniercaptoacetate (GDMA).

6. The composition of claim 1, wherein the at least one urease source is a watermelon seed.

7. The composition of claim 6, wherein the watermelon seed is a ground watermelon seed.

8. The composition of claim 7, wherein the ground watermelon seed has a particle size of about 425 µm or less.

9. The composition of claim 1, wherein the concentration of the polyhydroxy monomer, the borate ion source, the epoxy resin, the compound comprising one or more thiol groups, the urea and the urease source are each independently selected to control the rate of polymerization.

10. A method for temporal control of the induction time in a polymerization reaction, the method comprising:
(1) providing a first composition comprising: polyhydroxy monomer, and a borate ion source; or an epoxy resin, and a compound comprising one or more thiol groups;
(2) providing a second composition comprising urea and a urease source; and
(3) mixing the first composition and the second composition;
wherein the concentrations of one or more of the polyhydroxy monomers, the borate ion source, the compound comprising one or more thiol groups, the urea concentrations and urease source concentration are selected to temporally control induction time of the polymerization reaction.

11. The method of claim 10, wherein the polyhydroxy monomer is PVA.

12. The method of claim 10, wherein the borate ion source is boric acid.

13. The method of claim 10, wherein the epoxy resin is polyethylene glycol diglycidyl ether (PEGDGE).

14. The method of claim 10, wherein the compound comprising one or more thiol groups is ethoxylated trimethylolpropane tri(3-mercapto-propionate) (ETTMP).

15. The method of claim 10, wherein the at least one urease source is a watermelon seed.

16. The method of claim 15, wherein the watermelon seed is a ground watermelon seed.

17. The method of claim 16, wherein the ground watermelon seed has a particle size of about 425 µm or less.

18. The method of claim 10, wherein the ratio of the urea concentration to the at least one urease source concentration is about 3:100, about 1:30, about 3:70, about 1:20, about 3:50, about 3:40, about 3:30, about 3:20, or about 3:10.

19. The method of claim 10, wherein the at least one urease source is a ground watermelon seed, and the concentration of the urease is increased by decreasing the particle size of the ground watermelon seed.

20. A composition for forming a polymer comprising poly(vinyl) alcohol, a borate ion source, and a urease source.

21. The composition of claim 20, wherein the urease source is a watermelon seed.

* * * * *